United States Patent [19]

Bugle

[11] Patent Number: 5,027,998
[45] Date of Patent: Jul. 2, 1991

[54] CLAMPING MECHANISM FOR MAKING POROUS METAL COATED IMPLANT

[75] Inventor: Clifford M. Bugle, Library, Pa.

[73] Assignee: Dynamet, Inc., Washington, Pa.

[21] Appl. No.: 359,867

[22] Filed: Jun. 1, 1989

Related U.S. Application Data

[62] Division of Ser. No. 244,139, Sep. 14, 1988, Pat. No. 4,854,496, and Ser. No. 3,942, Jan. 16, 1987, abandoned.

[51] Int. Cl.$^5$ ............................................... A61F 1/24
[52] U.S. Cl. .................................... 228/44.5; 228/193
[58] Field of Search ................. 228/44.3, 44.5, 193; 623/18

[56] References Cited

U.S. PATENT DOCUMENTS

| | | | |
|---|---|---|---|
| 341,019 | 5/1886 | Kent | 228/44.5 |
| 3,400,872 | 9/1968 | Rogers | 228/44.5 |
| 4,089,456 | 5/1978 | Toppen et al. | 228/44.3 |
| 4,417,381 | 11/1983 | Higginbotham | 228/193 |
| 4,570,271 | 2/1986 | Sump | 623/18 |
| 4,636,219 | 1/1987 | Pratt | 228/193 |

*Primary Examiner*—M. Jordan
*Attorney, Agent, or Firm*—Webb, Burden, Ziesenheim & Webb

[57] ABSTRACT

A porous metal coated implant is produced by diffusion bonding metal powder particles, preferably spherical or flattened spherical metal powder particles of commercially pure titanium grade, in the form of an insert or pad to a substrate, preferably commercially pure titanium or Ti 6Al-4V ELI, a prosthesis, below the beta-transus of the substrate material, under pressure and temperature in a non-reactive atmosphere, such as vacuum. The use of pressure permits bonding temperatures to be reduced to approximately 50% of the melting point of the substrate material. A clamping mechanism for applying pressure to the components is also disclosed.

3 Claims, 4 Drawing Sheets

CLAMPING MECHANISM FOR MAKING POROUS METAL COATED IMPLANT

This application is a division of application Ser. No. 244,139, filed Sept. 14, 1988, now U.S. Pat. No. 4,854,496, which is a continuation of application Ser. No. 3,942, filed Jan. 16, 1987, now abandoned.

BACKGROUND OF THE INVENTION

1. Field of the Invention

This invention relates to porous metal coated implants, such as medical prostheses in the form of hip prosthesis consisting of an acetabular cup and a femoral stem, wherein a porous metal coating is applied to the surface of a metal substrate preconfigured in the form of the medical prosthesis. The implant according to the invention is produced by diffusion bonding metal powder particles in the form of an insert or pad to the substrate below the beta-transus of the substrate by applying suitable pressure and temperature in a non-reactive atmosphere. Preferably, the substrate is a reactive metal such as commercially pure titanium or a titanium base alloy, e.g., Ti 6Al-4V ELI and the powder insert is either commercially pure titanium or it may be a titanium alloy such as Ti 6Al-4V. The particles are further preferably in the form of an insert comprising powder spheres or spheres which have been flattened by removing a portion of each sphere to provide a bonding surface of increased area for contact to the surface of the substrate. The pressure is applied, preferably, by a novel clamping mechanism which is described hereinafter.

2. Brief Description of the Prior Art

Recently, titanium and titanium alloys have experienced increased acceptance as medical implant materials, especially for medical prosthesis such as orthopedic devices in the form of knee and hip joints. Of the available grades of titanium materials, commercially pure titanium and the Ti 6Al-4V ELI alloy have become the most commonly used for implants due to the exceptional combination of properties which they possess which include easy toleration by body tissues, corrosion resistance in body fluids, high strength, low modulus of elasticity and low density.

Despite the excellent mechanical properties of titanium, orthopedic implants of titanium materials do fail, commonly because of failure brought about by undesirable stresses induced in the implant caused by loosening or separation of the implant from the bone. This type of failure is especially typical for hip prostheses because of the cyclic loading and high stresses experienced in the hip joint.

To obviate the loosening failures, improved methods of fixation of the implant to the body bone or tissues have been employed, including the application of a porous coating to the surface of the implant which permits the bone cement or ideally the bone itself to penetrate the voids in the coating to establish and maintain a strong mechanical bond with the implant. The most commonly used porous coatings are gravity sintered spherical powder, diffusion bonded metal fiber, and plasma sprayed powder coating.

Gravity sintered spherical powder coatings of commercially pure titanium or titanium based alloys, such as Ti 6Al-4V, are available and processes for their application to reactive metal substrates in medical implants are known. One such process is disclosed and claimed in U.S. Pat. No. 4,612,160 entitled "Porous Metal Coating Process and Mold Therefor" by Alfred L. Donlevy and Clifford M. Bugle, which is assigned to the assignee of the present application. That process utilizes a rigid mold wherein the metal substrate or part thereof to be coated with metal powder is disposed in the mold, the assembly is presintered in the mold, and thereafter the coated substrate portion is removed from the mold and further sintered, the sintering being carried out in a non-reactive atmosphere, such as vacuum. The sintering of these coatings involves heating the assembly to temperatures approximating 85% of the melting point such that bonding of the powder particles to each other and to the metal substrate is achieved by solid state diffusion.

Diffusion bonded metal fiber coatings have been produced from titanium wire in the form of random porous fiber metal coatings and woven porous fiber metal coatings. These are well documented in the literature by P. Ducheyne et al. in "Titanium and Titanium Alloy Prostheses with Porous Fiber Metal Coatings," from *The Cementless Fixation of Hip Endoprosthesis*, ed. E. Morscher, copyright 1984 by Springer-Verlag Berlin Heidelberg and in publications of Zimmer entitled "Fatigue and Porous Coated Implants," copyright 1984 and "Mechanical Testing of Porous Implant Surfaces," copyright 1985. In the Ducheyne publication, it is reported that, in the case of woven fiber coatings, by using pressure as an activator during sintering, it is possible to lower the sintering temperature significantly and that pressure sintering of fiber titanium coatings onto a Ti-6%Al-4%V substrate has been successfully done at temperatures of 800° C.–925° C. which are below the $\alpha + \beta$ to $\beta$ transition temperature (975° C.).

Plasma spray coatings are produced from either commercially pure titanium or titanium alloy, such as Ti 6Al-4V. In this process material of the desired composition, usually in powder form, is melted in a plasma and propelled onto the substrate to be coated. Bonding is achieved by the impact and solidification of the molten particles on the substrate. As stated in U.S. Pat. No. 4,612,160, however, the known flame spray methods, illustrated for example by Hahn U.S. Pat. No. 3,605,123, are unattractive because pore size, volume and dimensional characteristics of the coating are difficult to control.

The mechanical property requirements of the acetabular cup and the femoral stem in a hip prosthesis are substantially different. Since the acetabular cup is primarily loaded in compression, a high fatigue limit is unnecessary since tensile stresses are required to produce fatigue failure. Moreover, since the acetabular cup is supported over most of its surface, there is minimal deflection of the cup and, therefore, high ductility is not essential.

On the other hand, the femoral stem of the hip prosthesis is cyclically loaded in such a manner that substantial tensile stresses are present in portions of the stem and, therefore, high tensile strength and a high fatigue limit are required to avoid failure of the implant. In addition, high ductility is required to permit the stem to flex under load and to transfer forces to the bone. The invention is particularly applicable, therefore, to the production of a femoral stem.

SUMMARY OF THE INVENTION

According to the present invention, a porous metal coated implant is produced by diffusion bonding metal powder particles, preferably spherical or flattened spherical metal powder particles of commercially pure titanium grade material, in the form of an insert or pad to a substrate, preferably of commercially pure (CP) titanium or titanium alloy, e.g., Ti 6Al-4V ELI, configured as a medical prosthesis such as a hip prosthesis consisting of an acetabular cup and a femoral stem, below the beta-transus of the substrate material, under pressure and temperature in a non-reactive atmosphere, such as vacuum. The use of pressure permits bonding temperatures to be reduced to approximately 50% of the melting point of the substrate material.

Preferably, the insert or pad is formed by molding in accordance with the teachings of U.S. Pat. No. 4,612,160. However, other methods of forming the insert, such as mixing the particles with a binder material or glue and/or forming adhesively bound particles into a large sheet from which individual inserts may be removed by die cutting or punching may be used.

The bonding pressure necessary may be applied by conventional means such as hot pressing or hot isostatic pressing, but is preferably applied through the use of a unique clamping mechanism which utilizes a first means such as plate members held or confined by second means such as elongated members, such as threaded rods or dowels, having different thermal expansion rates to apply pressure to the insert and substrate to bond the two together in a non-reactive atmosphere, such as vacuum, at a suitable temperature. The atmosphere may also be argon, helium or nitrogen.

Evaluation of porous coatings was performed wherein the data was reported by using the term "wrought" to refer to substrate material in the hot worked and annealed condition and the term "gravity sintered" to refer to coatings sintered at temperatures above the beta-transus temperature of the substrate material. Conversely, "diffusion bonded" denotes coatings which were bonded below the beta-transus of the substrate material. The beta-transus is that point where the crystalline structure changes from one form to another. In the case of Ti 6Al-4V ELI, the crystal structure changes from hexagonal to body centered cubic at a temperature in the range of about 1780°-1830° F., depending upon the exact chemical composition.

The test results demonstrated that porous coated implant components produced by the present diffusion bonding process achieved comparable porous coating bond strength to components produced by gravity sintering. However, although substrates subjected to both processes showed approximately 50% decrease in fatigue limit as compared to the wrought condition, the present diffusion bonding process significantly increased the tensile strength and ductility of the substrate when compared to the gravity sintering process.

DETAILED DESCRIPTION OF PRESENTLY PREFERRED EMBODIMENTS OF THE INVENTION

In the process according to U.S. Pat. No. 4,612,160, a substrate to be coated is cleaned and positioned in a rigid mold, of e.g. ceramic, metal or graphite material, having a defined mold cavity; the space between the mold cavity surface and the substrate is filled with a metal powder and the mold, powder and substrate assembly is presintered. The product produced in the mold is a metal powder coated substrate. In the present invention, powder particles are preferably molded to form an insert or pad without the substrate or the insert may be formed by mixing the particles with a binder material or glue or by other methods, such as by forming adhesively bound particles into a large sheet and cutting or removing individual inserts of the desired shape from the sheet.

Figure 1:
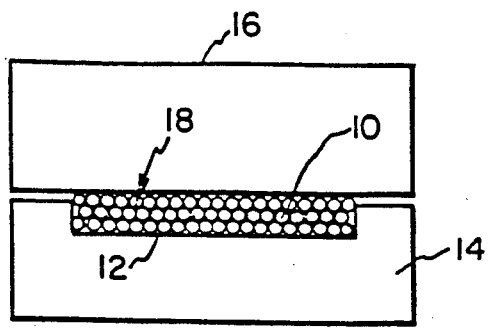
FIG. 1 is a cross section through a mold for presintering titanium metal powder particles for use as a porous coating insert according to the invention.

According to the preferred mode of practicing the present invention, as shown in FIG. 1 spherical powder 10 is placed in cavity 12 of a mold 14 which is closed by a cover 16. The mold 12 is preferably made from a graphite material. The mold cavity is configured to produce a porous metal shape in the form of a powder insert 18 of the desired configuration for a femoral stem 20 of a hip prosthesis, such as that shown in FIGS. 2 and 3, which has been forged and then machined with recesses 22 to receive porous inserts 18 made from powder 10.

The powder 10 is commercially pure titanium or titanium alloy powder and is commercially available, for example, from Nuclear Metals, Inc., Concord, Mass. However, other suitable powders may be used. The powder is screened to obtain a powder size between about 20 and 100 mesh, U.S. Standard Sieve, although any desired size may be used.

The powder is preferably processed in the same manner as set forth in U.S. Pat. No. 4,612,160, namely, the mold assembly consisting of mold 14 and cover 16 with the powder 10 therein is placed in a conventional muffle furnace having a protective, non-reactive atmosphere. The furnace is evacuated and the assembly heated to the proper temperature in the range of between about 1750° F. to about 2000° F. to presinter the powder to form a porous metal coating insert. The processing conditions in the mold described in U.S. Pat. No. 4,612,160 are incorporated by reference herein. The insert 18 is then removed from the mold and the insert is high temperature sintered to achieve particle bond strength and desired porosity prior to bonding to the stem. The temperatures used may range from 2200° F. to 2700° F. A surface 24 of the insert 18, hereinafter called the bonding surface, is placed in contact with a surface of the stem 20 for application of heat and pressure to the stem 20 and insert 18 to cause the insert to be diffusion bonded to the stem. The pressure and temperature are applied simultaneously in a non-reactive atmosphere, such as vacuum, sufficient pressure being applied to cause bonding at a temperature below the beta-transus. In the case of an insert of commercially pure titanium to be bonded to a substrate of Ti 6Al-4V ELI, the temperature used is approximately 1700° F. for about 30 to 90 minutes. The surface 28 of the insert 18 which is disposed in a recess 22 is preferably either flush with or extends slightly above the upper edge of recess 22, i.e., the outer surface of the stem 20.

Figure 2:
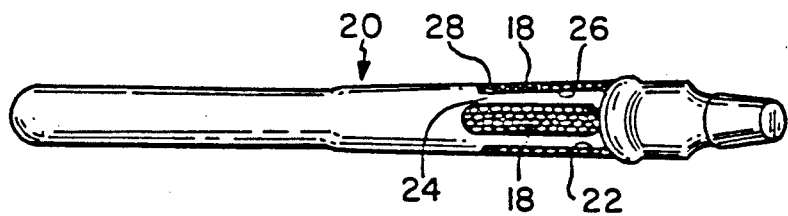
FIG. 2 is a top plan view of a femoral stem of a hip prosthesis having a porous coating of flattened spherical titanium powder particles diffusion bonded to a titanium alloy substrate and FIG. 2A is a photograph of the interface between the powder insert and the stem.
Figure 3:
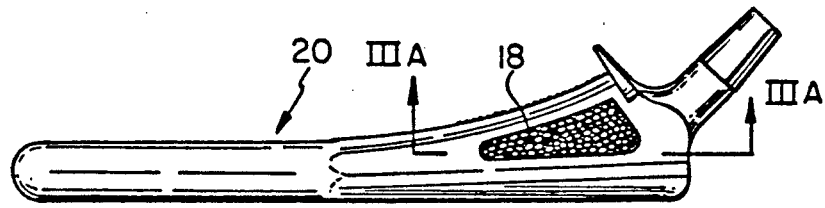
FIG. 3 is an elevational view of the femoral stem of FIG. 2
Figure 2A:
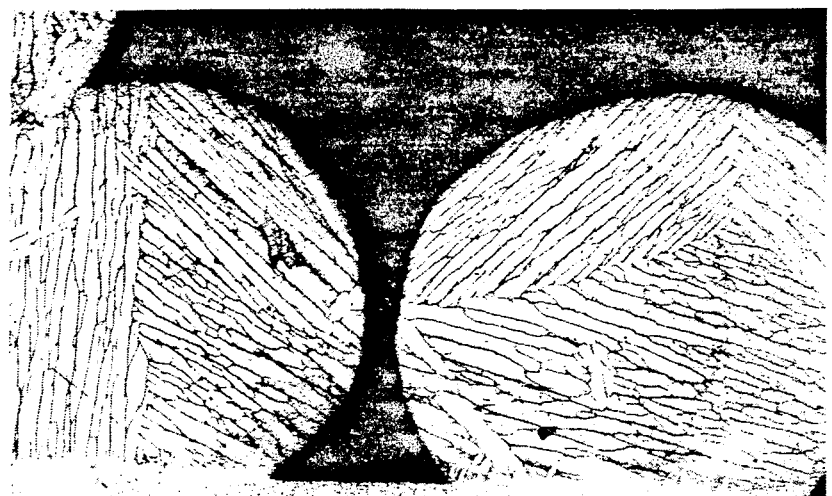

FIGS. 2 and 3 illustrate a femoral stem 20 having three inserts 18 formed of flattened spherical metal powder particles of commercially pure titanium bonded to a portion of the surface 26 of the femoral stem 20 of a hip prosthesis and disposed in recesses 22 premachined in the surface of the stem. The diffusion bond between commercially pure flattened spherical particles (−25 +35 mesh powder) of the insert and a stem of Ti 6Al-4V ELI is clearly illustrated in FIG. 2A.

Figure 3A:
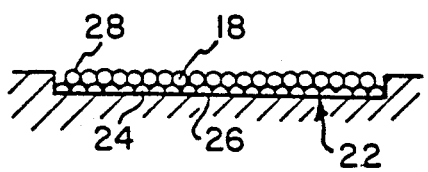
FIG. 3A is an enlarged partial sectional view taken along lines IIIA—IIIA of FIG. 3 showing the interface between the insert and the stem.
Figure 4:
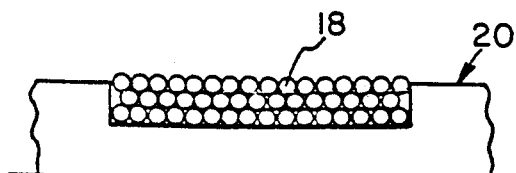
FIG. 4 is an enlarged partial elevational view of a portion of a femoral stem having a porous coating insert of spherical titanium powder particles diffusion bonded to a titanium alloy substrate and FIG. 4A is a photograph of the interface between the particle insert and the stem.
Figure 4A:
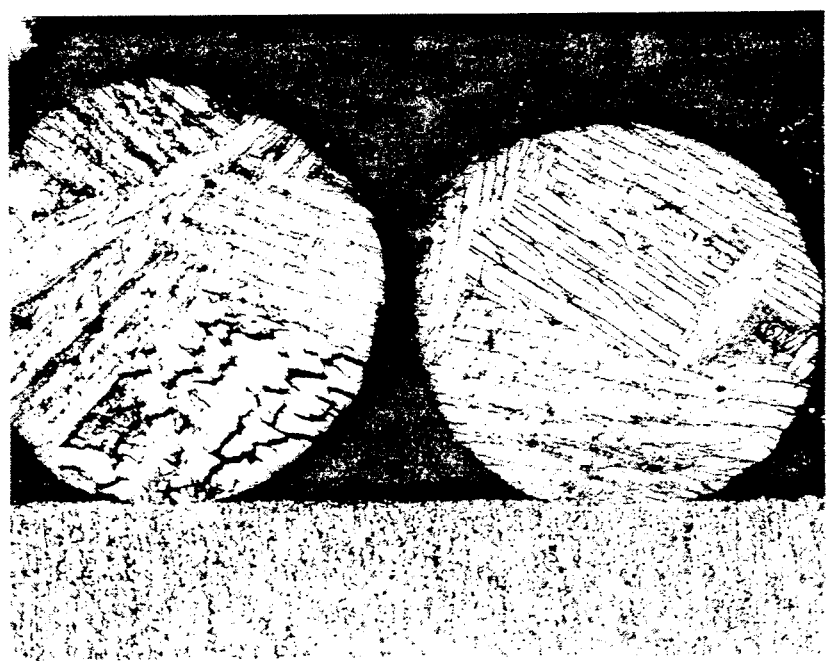

The powder insert 18 may, of course, consist of spherical particles as shown in FIG. 4. A diffusion bonded joint is shown in FIG. 4A between commercially pure titanium particles (−25 +35 mesh) and a stem of Ti 6Al-4V ELI. However, it has been found that an improvement in the bond between the powder insert 18 and the stem 20 results from initially flattening each of the spherical powder particles 10 by mechanical, chemical or electrical means to form the bonding surface 24. For example, a portion of each sphere may be removed mechanically by the use of emery paper, sand paper, surface grinding, milling, filing or the like. Acid may be used to chemically remove a portion of the spherical particles or electrical discharge means may be employed. By flattening the spheres, the contact area between the powder particles of the bonding surface and the substrate or component is increased as shown in the enlargement of FIG. 3A, thus increasing the load carrying capacity of the bond between the insert and the stem since it is known that, for a straight rod:

Load Carrying Capacity=(Failure Stress)(Contact Area)

Hence, it is possible to influence the load carrying capacity of the bond by adjusting the area of contact between the components which are bonded. As an ideal, the load carrying capacity can be increased to approximately 65% of that of a solid having the same outside diameter; however, a limit is reached when failure occurs between powder particles and any further improvement requires an appropriate adjustment in sintering parameters.

Although, theoretically, the thickness of the insert is not critical, those medical people working in the biological field have judged a preferable thickness to be in the approximate range of 0.045 to 0.055 inches. Of course, the application of pressure to an insert comprised of spheres does tend to flatten the spheres to some extent.

After the insert is flattened on one surface 24, the surface is cleaned, preferably ultrasonically, to remove any debris, chips and/or dirt which would be detrimental to the bonding of the insert 18 to the stem 20. Thereafter, each insert 18 is placed in a recess 22 in the stem.

Various methods may be used to apply pressure to the insert 18 and stem 20 to cause bonding of the two components. Such methods include clamping, hot pressing and hot isostatic pressing. The significant feature is that powder particles be in the form of an insert prior to the application of the required pressure and heat. A preferred clamping mechanism is described hereinafter in connection with FIGS. 5 and 6 of the drawings.

Figure 5:
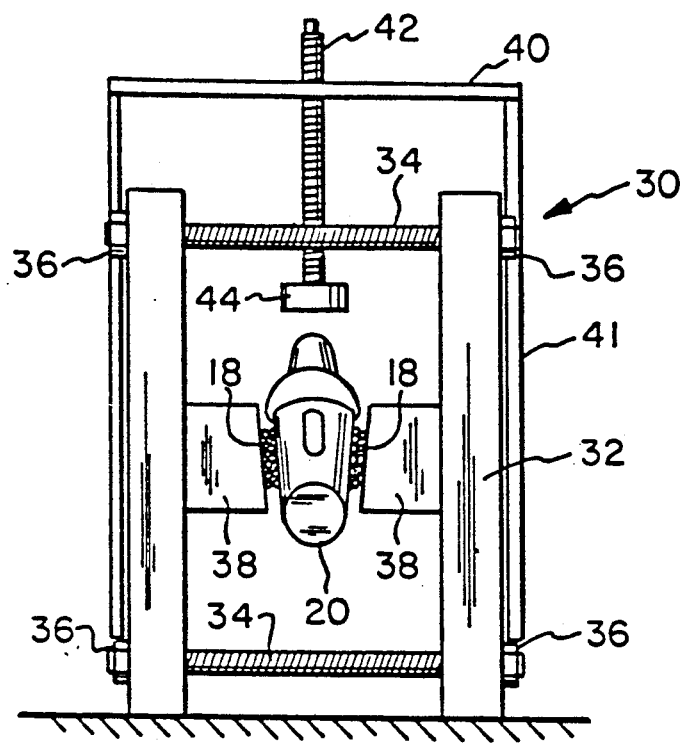
FIG. 5 is an end elevational view of a clamping mechanism for applying pressure to the insert and substrate during bonding.
Figure 6:
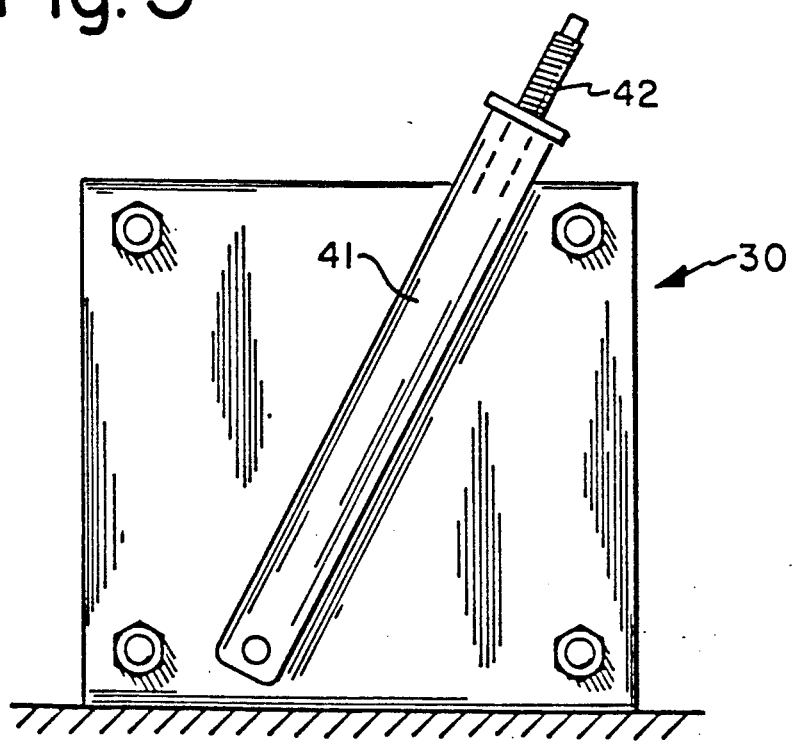
FIG. 6 is a side elevational view of the clamping mechanism of FIG. 5.

The clamping mechanism which is preferred is illustrated in FIGS. 5 and 6. Essentially the clamping mechanism 30 comprises a pair of plate members 32 preferably of Inconel 718, a high temperature material having high thermal expansion characteristics, connected by a plurality of elongated members, usually four cylindrical rods 34, having threads to which nuts 36 are engaged. The rods and nuts are preferably made of molybdenum which has a relatively low coefficient of thermal expansion when compared to I-718. A pair of graphite blocks 38 are secured to the inside surfaces of plates 32 for engagement with the titanium inserts 18 to be bonded to the surfaces on the sides of the titanium or titanium alloy stem 18 of an implant. Since the expansion rates of titanium and I-718 are both greater than the expansion rate of molybdenum, when the clamping mechanism with the insert and the stem is heated to temperature, pressure is applied to the insert to cause diffusion bonding of the insert and substrate in accordance with the invention.

The clamping mechanism 30 may also include a bridge 40 extending on brackets 41 normal to the opposed plate members 32. A graphite block 44 is provided on an end of the rod 42 for engagement with insert 18 on the upper surface of the stem 20, normal to the inserts 18 engaged by blocks 38, for bonding of that insert to the stem.

After the bonding is complete, the shiny appearance of the surface of the titanium insert 18 may be enhanced by cleaning the insert manually with a titanium bristled brush, reheating the assembly without the application of pressure at about 1700° F. for about ½ hour.

Figure 7:
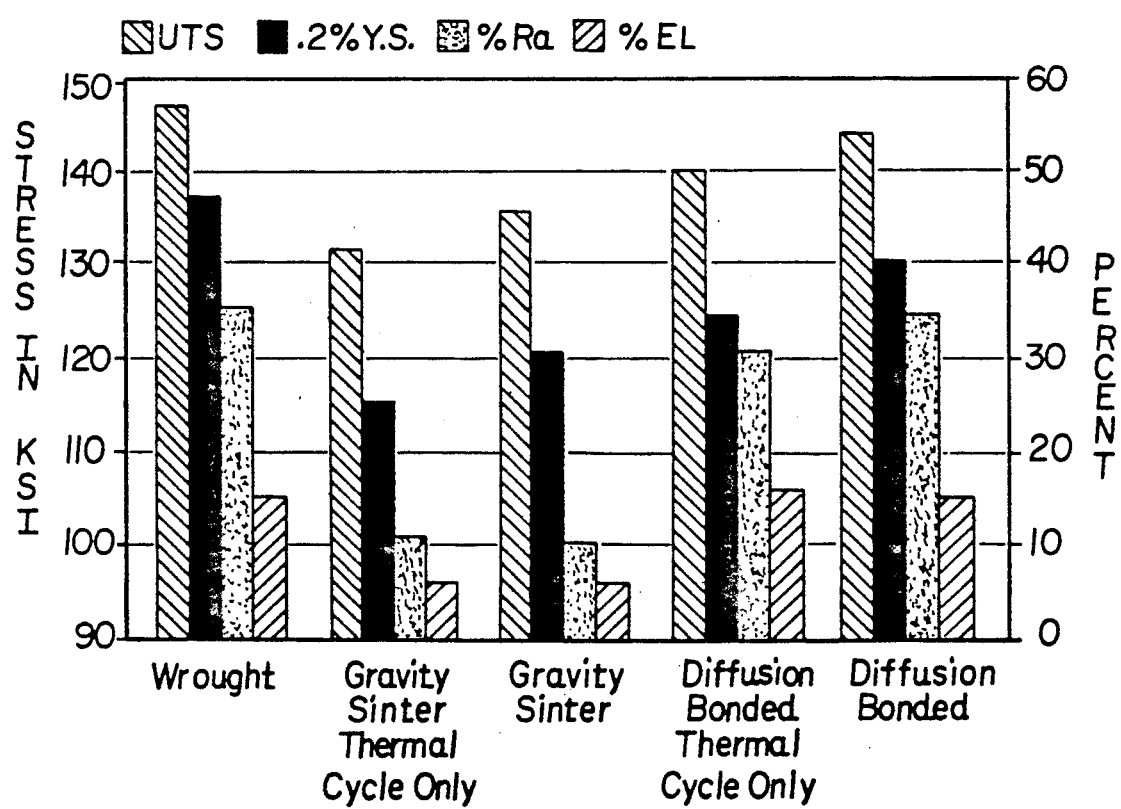
FIG. 7 is a Table of test results.

A series of tests was made to determine the tensile strength of diffusion bonded porous coatings comprised of spherical and flattened powder particles with and without the substrate. The results of those tests were then compared with wrought and gravity sintered coatings prepared in accordance with the teachings of U.S. Pat. No. 4,612,160. The comparison is illustrated in the Table shown in FIG. 7.

EXAMPLE I tensile specimens of porous coated substrates according to the following conditions were prepared according to standard practices:

| Thermal Condition | Substrate Material | Porous Coating Material |
|---|---|---|
| 1. Wrought | Ti 6Al-4V ELI | None |
| 2. Gravity Sintered | Ti 6Al-4V ELI | Ti 6Al-4V spherical powder (−30 +40 mesh, 420–600 microns) |
| 3. Diffusion Bonded | Ti 6Al-4V ELI | CP Ti grade II flattened spherical powder (−30 +40 mesh, 420–600 microns) |

Each specimen was acid cleaned to remove all machining fluids, dirt and other contaminants from the substrate surface. The porous coating material was then applied to the substrate. Gravity sintered specimens were carefully transferred into the vacuum furnace where they were sintered at a temperature of approximately 85% of the melting point of the substrate. This sintering temperature is above the beta-transus temperature, which for Ti 6Al-4V ELI is about 1800° F. Diffusion bonded specimens were subjected to heat and pressure in the clamping mechanism described above. The bonding was carried out in a vacuum ($10^{-5}$ torr) at a temperature of approximately 50% of the melting point of the substrate. This temperature is below the beta-transus.

Plate specimen geometries, 0.17 inches thick, were utilized for all tensile specimens. This geometry was selected because it simplified the diffusion bonding process.

In the Table is a comparison of the tensile test results on the specimens given in Example I, wherein UTS means Ultimate Tensile Strength, YS means, Yield Strength, % Ra means Reduction of Area and % El means Percent Elongation.

Tensile properties of the wrought, gravity sintered and diffusion bonded specimens are also presented in the Table. The wrought material has an UTS of 147 KSI, a 0.2% YS of 137 KSI and % Ra and % El of 37% and 16% respectively. These data demonstrate a good combination of high strength and high ductility. Subsequent porous coating processing causes a degradation of the wrought substrate tensile properties.

Overall tensile properties of the gravity sintered specimens were significantly decreased by the sintering process. A 9 and 15 KSI drop was realized in the UTS and 0.2% YS respectively. Also, the ductility measurements decreased to one third of their wrought levels. This change in properties may be attributed to the extremely large grain size and the continuous alpha layer at the grain boundary.

Specimens subjected to the diffusion bonding process also displayed a decrease in tensile properties when compared to the wrought condition. However, this decrease in properties is minimal compared to that suffered by the gravity sintered condition. A 3 to 4 KSI decrease in UTS and 0.2% YS was measured. Reduction of area fell by 3% with no change in the elongation. Comparison of the diffusion bonded and the wrought microstructures showed the grain coarsening effect of the diffusion bonding process. This slightly larger grain size led to the observed decrease in tensile properties.

From the Table it is evident that the ultimate tensile strength of the diffusion bonded porous coated substrate substantially exceeds the ultimate tensile strength of the gravity sintered porous coated substrate and nearly approaches the ultimate tensile strength of the wrought material. In addition, the diffusion bonded porous coated substrate according to the invention has substantially greater yield strength, area reduction and percent elongation when compared to the gravity sintered specimens. This means that the gravity sintered porous coated substrate tends to be more brittle, deflects less and will tend to fail when used as an implant, whereas the diffusion bonded porous coated substrate will deflect (Ra) until it hits the bone and will tend to be supported by the bone.

By diffusion bonding a spherical or flattened spherical metal powder coating of commercially pure titanium or titanium alloy on a substrate, especially in the form of a femoral stem of a hip prosthesis, improved tensile strength characteristics are achieved when compared to gravity sintered porous coated implants.

EXAMPLE II

To compare diffusion bonded porous coatings of spherical powder particles with diffusion bonded porous coatings of flattened spherical powder particles, eight porous metal specimens comprising a solid substrate with a porous coating were prepared. Each specimen was commercially pure titanium having −25 +35 mesh. Each was diffusion bonded at a temperature of 1700° F. for 30 minutes in vacuum. A torque of 15 inch-pounds was applied. The test results were as follows:

| Specimen No. | Type | Grade | Initial Diameter | Initial Area | Ultimate Load (#) | Bond Strength (psi) |
|---|---|---|---|---|---|---|
| 1 | Spherical | 4 | .489 | .1878 | 1430 | 7614 |
| 2 | Flat | 4 | .490 | .1886 | 2620 | 13891 |
| 3 | Spherical | 1 | .489 | .1878 | 1100 | 5857 |
| 4 | Flat | 1 | .489 | .1878 | 2240 | 11927 |
| 5 | Spherical | 4 | .489 | .1878 | 1360 | 7241 |
| 6 | Flat | 4 | .490 | .1886 | 3620 | 19194 |
| 7 | Spherical | 1 | .489 | .1878 | 1300 | 6922 |
| 8 | Flat | 1 | .490 | .1886 | 2100 | 11134 |

From the foregoing data, it is apparent that the joints between a substrate and the inserts made of flattened powder spheres had increased load carrying capacity when compared to joints between a substrate and spherical powder inserts.

Having described presently preferred embodiments of the invention, it is to be understood that it may otherwise be embodied within the scope of the appended claims.

I claim:

1. A clamping mechanism for applying pressure to two components to cause them to bond together under the influence of temperature comprising:
   (a) first means comprising opposed plate members of Inconel material for clamping the components to be bonded therebetween;
   (b) second means comprising elongated members of molybdenum material for confining the first means about the components whereby, upon application of heat to the means and to the components, the components are diffusion bonded to one another under pressure produced by the different coefficients of expansion of the Inconel and molybdenum materials;
   (c) bridge means normal to said opposed plate members;
   (d) a member threaded through a tapped hole in said bridge means; and
   (e) a graphite block on an end of said member for engagement with a third component to be bonded to one of said first two components under heat and pressure.

2. A clamping mechanism as set forth in claim 1 and including a graphite block on a surface of each plate member and adapted to contact one of the components to be bonded.

3. A clamping mechanism as set forth in claim 1 or claim 2 wherein said two components are made of titanium based material.

* * * * *